United States Patent
Zhu et al.

(10) Patent No.: US 11,117,866 B2
(45) Date of Patent: Sep. 14, 2021

(54) TERPINEOL AND PREPARATION METHOD AND APPLICATION THEREOF

(71) Applicant: ZHEJIANG ACADEMY OF TRADITIONAL CHINESE MEDICINE, Hangzhou (CN)

(72) Inventors: Wanping Zhu, Hangzhou (CN); Yongzhou Hu, Hangzhou (CN); Xia Liu, Hangzhou (CN); Fanzhi Kong, Hangzhou (CN); Yuji Wang, Hangzhou (CN)

(73) Assignee: ZHEJIANG ACADEMY OF TRADITIONAL CHINESE MEDICINE, Hangzhou (CN)

( * ) Notice: Subject to any disclaimer, the term of this patent is extended or adjusted under 35 U.S.C. 154(b) by 455 days.

(21) Appl. No.: 16/074,403

(22) PCT Filed: Jan. 16, 2017

(86) PCT No.: PCT/CN2017/071217
§ 371 (c)(1),
(2) Date: Jul. 31, 2018

(87) PCT Pub. No.: WO2017/133429
PCT Pub. Date: Aug. 10, 2017

(65) Prior Publication Data
US 2019/0337900 A1    Nov. 7, 2019

(30) Foreign Application Priority Data
Feb. 4, 2016    (CN) .......................... 201610079970.4

(51) Int. Cl.
| | |
|---|---|
| *C07D 221/00* | (2006.01) |
| *A61P 9/12* | (2006.01) |
| *C07C 69/24* | (2006.01) |
| *C07C 203/04* | (2006.01) |
| *C07C 229/12* | (2006.01) |
| *C07C 323/52* | (2006.01) |
| *C07D 263/04* | (2006.01) |

(52) U.S. Cl.
CPC ............. *C07D 221/00* (2013.01); *A61P 9/12* (2018.01); *C07C 69/24* (2013.01); *C07C 203/04* (2013.01); *C07C 229/12* (2013.01); *C07C 323/52* (2013.01); *C07D 263/04* (2013.01)

(58) Field of Classification Search
CPC ...................................................... C07D 221/00
USPC ...................................................... 514/239.2
See application file for complete search history.

(56) References Cited

FOREIGN PATENT DOCUMENTS

| | | |
|---|---|---|
| CN | 102416154 | 4/2012 |
| CN | 103922927 | 7/2014 |
| WO | WO2013034416 | 3/2013 |

OTHER PUBLICATIONS

Bian, Rulian et al., "The Pharmacological Properties of a New Antiasthmatic Drug, a-Terpineol", Chinese Pharmacological Bulletin, vol. 3, No. 6, Dec. 31, 1987, ISSN 1001-1978, p. 323 and 326.

*Primary Examiner* — Taofiq A Solola
(74) *Attorney, Agent, or Firm* — Jiwen Chen; Jacobson Holman PLLC

(57) ABSTRACT

The present invention discloses a terpinenol compound as well as its preparation method and application. The structure of such terpinenol compound is as shown in Formula (I) or (II). In Formula (I), R is independently selected from $C_{12}$-$C_{16}$ alkyl, —$NR^1R^2$, —$SR^3$ or —$OR^4$; $R^1$, $R^2$, $R^3$ and $R^4$ are independently selected from $C_1$-$C_6$ alkyl or —$NO_2$; the $C_1$-$C_6$ alkyl can be substituted by OH; Alternatively, the $R^1$ and $R^2$ form a five-member ring or six-member ring in together with N used to link up them; the five-member or six-member ring may contain one O or C=O. As indicated by results of activity test, such terpinenol compound has satisfactory effect in prevention of asthma, inflammation and pulmonary artery hypertension, which also has high pharmaceutical significance.

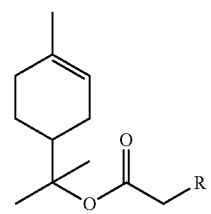

(I)

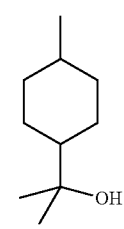

(II)

4 Claims, No Drawings

TERPINEOL AND PREPARATION METHOD AND APPLICATION THEREOF

This is a U.S. national stage application of PCT Application No. PCT/CN2017/071217 under 35 U.S.C. 371, filed Jan. 16, 2017 in Chinese, claiming priority of Chinese Application No. 201610079970.4, filed Feb. 4, 2016, all of which are hereby incorporated by reference

FIELD OF THE INVENTION

The present invention is related to the biomedicine field, in particular to a terpinenol compound and its preparation method and application.

BACKGROUND ARTS

Blumea oil belongs to a volatile oil as contained in the dry or fresh leaf of *Artemisia argyi*, which can directly slacken tracheal smooth muscle, and guard against convulsion to the tracheal smooth muscle and asthma as incurred by antigen, acetylcholine and histamine. It also has anti-allergic effect to inhibit allergic slow reacting substance (SRS-A) released by sensitized lung tissue, and guard against SRS-A and 5-hydroxy tryptamine. It is also available for phlegm elimination and cough suppression. It exerts no excitation to the heart, which is mainly used for therapy of bronchial asthma and asthmatic chronic bronchitis.

Alpha-terpinenol is an active ingredient extracted from the Blumea oil for asthma suppression, of which chemical designation is α,α,4-Trimethylcyclohex-3-en-1-methanol. According to pharmacological action of α-terpinenol reported by Bian Rulian and his colleagues ("a new antiasthmatic drug-pharmacological action of α-terpinenol", Chinese Pharmacological Bulletin, Page 323-328, Vol. 3, No. 6, 1987), α-terpinenol is available for air passage relaxation during in vivo experiment and experiment in vitro to guinea pig, which can increase cAMP content in the tracheal smooth muscle; it also plays a role of anti-anaphylaxis, cough suppression and phlegm elimination, which is a safe and effective new antiasthmatic drug owing to its low toxicity. As different from β receptor agonist, α-terpinenol has inhibiting effect on isolated atria of guinea pig.

Chinese Patent Application with the publication number of CN 103922927 A discloses a derivative of α-terpinenol as well as its preparation method and application; structure of such derivative of α-terpinenol is shown as follows:

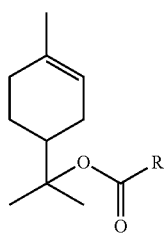

Wherein, R is selected from $C_1\sim C_5$ alkyl; however, the anti-asthmatic activity is not satisfactory despite of the fact that it has been enhanced to some extent through derivatization of α-terpinenol.

SUMMARY OF THE INVENTION

The present invention provides an α-terpinenol compound as well as its preparation method and application; such terpinenol compound has higher anti-asthmatic activity and anti-inflammation activity.

An anti-asthmatic compound, of which structure is as shown in Formula (I) or (II):

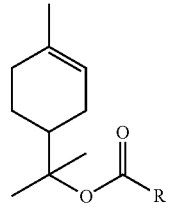

(I)

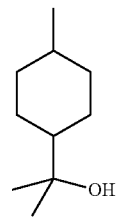

(II)

In Formula (I), R is independently selected from $C_{12}\sim C_{16}$ alkyl, —NR$^1$R$^2$, —SR$^3$ or —OR$^4$;

R$^1$, R$^2$, R$^3$ and R$^4$ are independently selected from $C_1\sim C_6$ alkyl or —NO2; the $C_1\sim C_6$ alkyl can be substituted by OH;

Alternatively, the R$^1$ and R$^2$ form a five-member ring or six-member ring in together with N used to link up them; the five-member or six-member ring may contain one O or C=O.

As indicated by activity test, the terpinenol compound according to the present invention can slacken the tracheal smooth muscle, and reduce the inflammatory cell, which can also effectively alleviate pulmonary hypertension.

In a preferred embodiment, the R is —NR$^1$R$^2$; in such case, the terpinenol compound can form a medically acceptable salt with acids to facilitate dissolution in the water and pharmaceutical application.

In a preferred embodiment, the R is $C_{12}H_{25}$, $C_{16}H_{33}$ or one of the following functional groups:

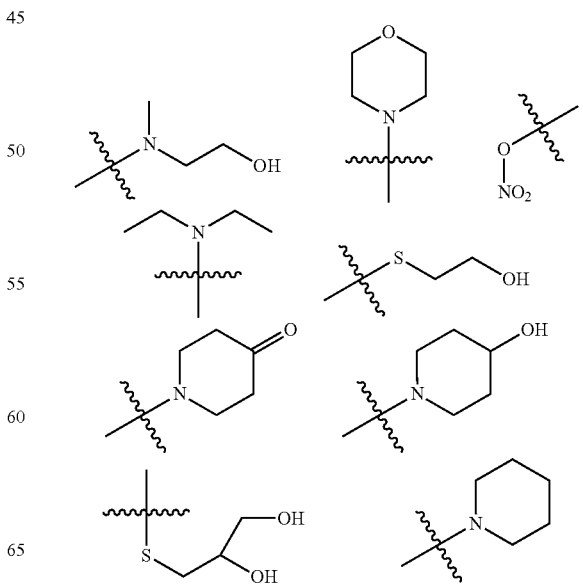

3

-continued

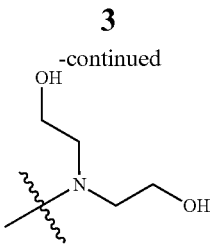

Wherein, "⁓" refers to link location.

Such functional groups can ensure higher activity and easy acquisition of compound.

The present invention further provides a method for preparation of the terpinenol compound.

When the terpinenol compound is the compound as shown in Formula (I), and R is $C_{12}$~$C_{16}$ alkyl, the preparation method comprises the following steps:

Obtaining the terpinenol compound through a reaction between the α-terpinenol and alkyl chloride in the dichloromethane under the action of pyridine;

The alkyl chloride is C14~C16 alkyl chloride.

When the terpinenol compound is the compound as shown in Formula (I), and R is —$NR^1R^2$, —$SR^3$ or —$OR^4$; such preparation method comprises the following steps:

(1) Obtaining the esterified intermediate through a reaction between the α-terpinenol and bromoacetyl bromide in the dichloromethane under the action of pyridine;

(2) Obtaining the terpinenol compound through a substitution reaction between the esterified intermediate as obtained in Step (1) and a nucleophilic reagent in the acetonitrile under the action of inorganic base;

The nucleophilic reagent is $HNR^1R^2$, $HSR^3$ or $HOR^4$.

When the terpinenol compound is the compound as shown in Formula (II), the preparation method comprises the following steps:

Obtaining the terpinenol compound through hydrogenation of α-terpinenol in the methanol in the atmosphere of Pd/C and hydrogen gas;

The present invention further provides an application of the terpinenol compound in pharmaceutical field.

In a preferred embodiment, the terpinenol compound is used to prepare anti-asthmatic drug;

The anti-asthmatic drug is used to relax bronchus.

As indicated by testing results, the terpinenol compound can also effectively reduce inflammatory cells. In a further preferred embodiment, the terpinenol compound is used to prepare anti-inflammatory drug.

In still a further preferred embodiment, the terpinenol compound is used to prepare drugs for therapy or alleviation of pulmonary hypertension.

As compared with prior arts, the present invention has the following beneficial effect:

(1) The present invention has effectively improved the role of such compound in guarding against asthma and pulmonary hypertension through derivatization of terpinenol compound;

(2) The terpinenol compound according to the present invention can reduce inflammatory cells, which has higher anti-inflammation activity.

SPECIFIC EMBODIMENTS OF THE INVENTION

Embodiment 1

α-terpinenol (4 mmol) taken by precise weighing was dissolved in 10 ml dichloromethane, and (6 mmol) pyridine

4 was added, then myristoyl chloride (6 mmol) was added subjecting to ice bathing for reaction for 8 hours at room temperature to obtain the final product 2a (3.74 mmol, yield rate of 93.5%). Product structure is as follows:

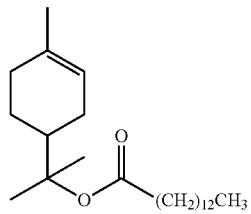

Embodiment 2

α-terpinenol (4 mmol) taken by precise weighing was dissolved in 10 ml dichloromethane, and (6 mmol) pyridine was added, then Octadecanoyl chloride (6 mmol) was added subjecting to ice bathing for reaction for 8 hours at room temperature to obtain the final product 2b (3.86 mmol, yield rate of 96.5%).

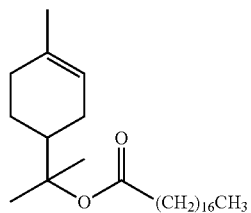

Embodiment 3-12

(1) 1.85 g (10 mmol) α-terpinenol was taken by weighing, and was put into 50 ml round-bottom flask; 30 ml dichloromethane and 1.91 ml (20 mmol) pyridine were further added, then 2.09 ml (20 mmol) bromoacetyl bromide was added subjecting to ice bathing for reaction at room temperature for 7 hours to obtain intermediate 3 (5.9 mmol, yield rate of 48.2%).

Reaction equation is stated as follows:

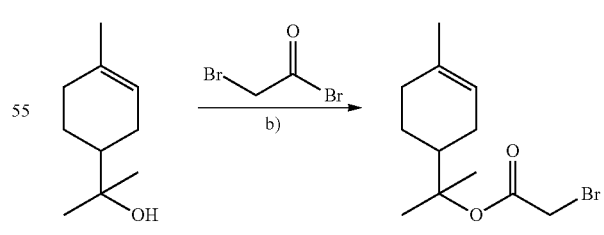

(2) Intermediate 3 (274 mg, 1 mmol) was dissolved in 10 mL acetonitrile, and potassium carbonate (276.4 mg, 2 mmol) and intermediate 4 (2 mmol) were added at room temperature to obtain product 5; structure and yield rate of intermediate 4 were as shown in Table 1.

TABLE 1

Substrate in Embodiment 3-12 and Results

| Embodiment | Intermediate 3 | Yield | Yield Coefficient |
|---|---|---|---|
| 3 | 4a | 0.765 mmol | 76.5% |
| 4 | 4b | 0.842 mmol | 84.2% |
| 5 | 4c | 0.748 mmol | 74.8% |
| 6 | 4d | 0.914 mmol | 91.4% |
| 7 | 4e | 0.839 mmol | 83.9% |
| 8 | 4f | 0.812 mmol | 81.2% |
| 9 | 4g | 0.828 mmol | 82.8% |
| 10 | 4h | 0.87 mmol | 87% |
| 11 | 4i | 0.873 mmol | 87.3% |
| 12 | 4j | 0.635 mmol | 63.5% |

Embodiment 13

α-terpinenol (400 mg) was added into 10 mL methanol, and Pd/C (40 mg) was further added for agitation in the hydrogen environment for 8 hours. Colorless oily substance 6 (38 mg, 93.5%) was obtained through separation. Reaction equation is as follows:

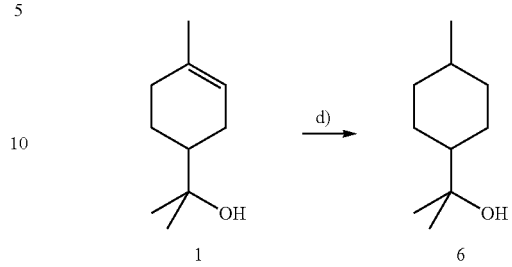

Data on structural characteristics of some compounds is as follows:

Compound A

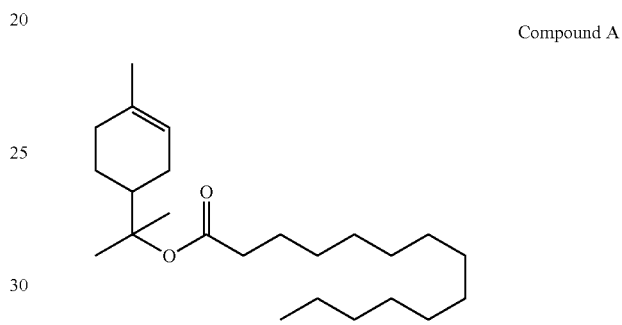

1H NMR (500 MHz, CDCl$_3$): δ 5.37 (s, 1H), 2.25-2.16 (m, 2H), 2.07-1.90 (m, 4H), 1.89-1.76 (m, 2H), 1.64 (s, 3H), 1.61-1.52 (m, 2H), 1.43 (s, 3H), 1.41 (s, 3H), 1.25 (s, 21H), 0.91-0.82 (m, 3H).

Compound B

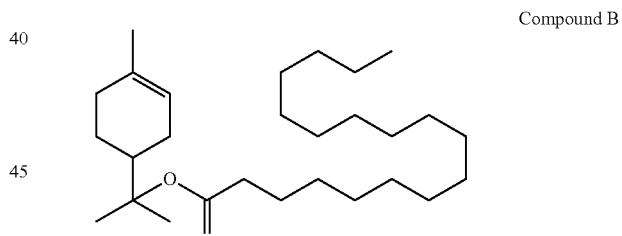

1H NMR (500 MHz, CDCl$_3$): δ 5.36 (dd, J=8.3, 6.9 Hz, 1H), 2.20 (t, J=7.5 Hz, 2H), 2.08-1.91 (m, 4H), 1.88-1.75 (m, 2H), 1.64 (s, 3H), 1.58-1.53 (m, 2H), 1.44 (s, 3H), 1.41 (s, 3H), 1.34-1.19 (m, 29H), 0.88 (t, J=7.0 Hz, 3H).

Compound C

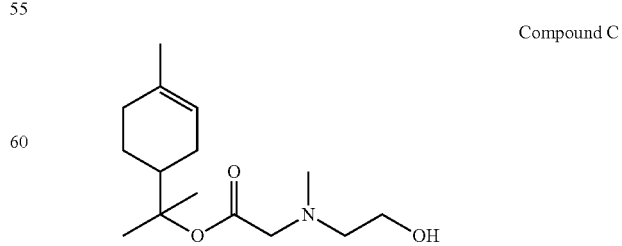

1H NMR (500 MHz, CDCl$_3$): δ 5.38 (d, J=2.0 Hz, 1H), 3.62-3.58 (m, 2H), 3.24 (s, 2H), 2.73-2.69 (m, 2H), 2.44 (s,

3H), 2.13-1.93 (m, 4H), 1.89-1.76 (m, 2H), 1.66 (s, 3H), 1.49 (s, 3H), 1.46 (s, 3H), 1.32 (tt, J=10.4, 5.3 Hz, 1H).

Compound D

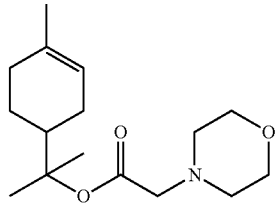

1H NMR (500 MHz, CDCl$_3$): δ 5.38 (dd, J=3.1, 1.7 Hz, 1H), 3.78 (dd, J=8.3, 3.6 Hz, 4H), 3.13 (d, J=1.3 Hz, 2H), 2.64-2.56 (m, 4H), 2.12-1.92 (m, 4H), 1.89-1.76 (m, 2H), 1.66 (s, 3H), 1.48 (s, 3H), 1.45 (s, 3H), 1.36-1.26 (m, 1H).

Compound E

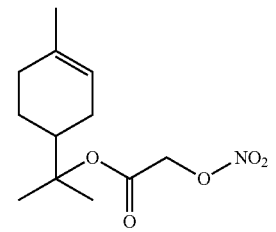

1H NMR (500 MHz, CDCl$_3$): δ 5.36 (s, 1H), 3.75 (s, 2H), 2.13-1.94 (m, 4H), 1.92-1.76 (m, 2H), 1.64 (s, 3H), 1.45 (s, 3H), 1.36 (s, 3H), 1.33 (qd, J=12.3, 5.6 Hz, 1H).

Compound F

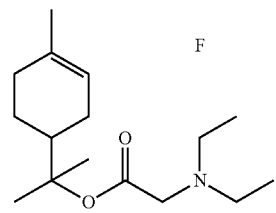

1H NMR (500 MHz, CDCl$_3$): 5.38 (dd, J=2.9, 1.5 Hz, 1H), 3.23 (s, 2H), 2.67 (q, J=7.3 Hz, 4H), 2.10-1.93 (m, 4H), 1.88-1.76 (m, 2H), 1.65 (s, 3H), 1.47 (s, 3H), 1.44 (s, 3H), 1.35-1.25 (m, 1H), 1.08 (td, J=7.2, 4.1 Hz, 6H).

Compound G

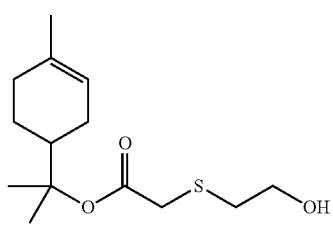

1H NMR (500 MHz, CDCl$_3$): δ 5.37-5.34 (m, 1H), 3.75 (t, J=5.6 Hz, 2H), 3.18 (s, 2H), 2.81 (t, J=5.5 Hz, 2H), 2.09-1.94 (m, 4H), 1.86-1.76 (m, 2H), 1.63 (s, 3H), 1.45 (s, 3H), 1.43 (s, 3H), 1.35-1.25 (m, 1H);

Compound H

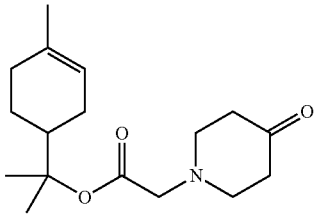

1H NMR (500 MHz, CDCl$_3$): δ 5.33 (t, J=8.9 Hz, 1H), 3.24 (s, 2H), 2.87 (t, J=6.1 Hz, 4H), 2.48 (t, J=6.1 Hz, 4H), 2.09-1.89 (m, 4H), 1.86-1.73 (m, 2H), 1.63 (s, 3H), 1.46 (s, 3H), 1.43 (s, 3H), 1.34-1.25 (m, 1H);

Compound J

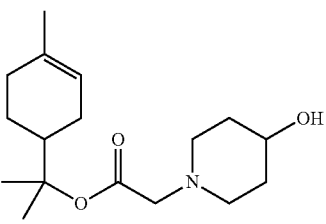

1H NMR (500 MHz, CDCl$_3$): δ 5.35 (d, J=2.1 Hz, 1H), 3.73-3.66 (m, 1H), 3.11 (s, 2H), 2.81 (td, J=8.9, 3.8 Hz, 2H), 2.38-2.30 (m, 2H), 2.10-1.88 (m, 4H), 1.85-1.74 (m, 2H), 1.68-1.58 (m, 6H), 1.45 (s, 3H), 1.42 (s, 3H), 1.33-1.26 (m, 1H);

Compound K

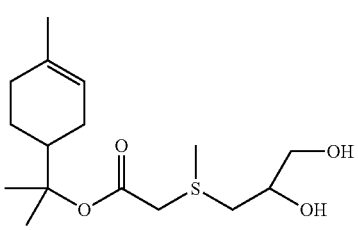

1H NMR (500 MHz, CDCl$_3$): δ 5.35 (s, 1H), 3.81 (s, 1H), 3.71 (d, J=11.0 Hz, 1H), 3.60-3.46 (m, 1H), 3.27-3.15 (m, 2H), 2.85-2.77 (m, 1H), 2.68 (dd, J=14.0, 8.4 Hz, 1H), 2.09-1.90 (m, 4H), 1.86-1.75 (m, 2H), 1.63 (s, 3H), 1.45 (s, 3H), 1.43 (s, 3H), 1.33-1.25 (m, 1H);

Compound L

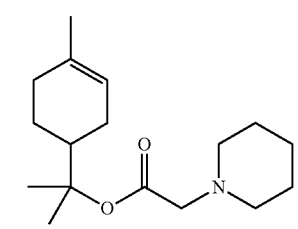

1H NMR (500 MHz, CDCl$_3$): δ 5.42-5.33 (m, 1H), 3.06 (d, J=1.2 Hz, 2H), 2.55-2.43 (m, 4H), 2.10-1.89 (m, 4H), 1.86-1.71 (m, 2H), 1.62 (s, 3H), 1.59 (dd, J=11.3, 5.7 Hz, 4H), 1.43 (d, J=5.8 Hz, 3H), 1.42-1.37 (m, 5H), 1.27 (ddd, J=24.4, 12.2, 5.7 Hz, 1H);

Compound M

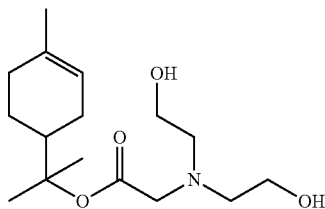

1H NMR (500 MHz, CDCl₃): δ 5.33 (s, 1H), 3.56-3.54 (m, 1H), 3.11 (s, 2H), 2.81 (td, J=8.9, 3.8 Hz, 2H), 2.38-2.30 (m, 2H), 2.10-1.88 (m, 4H), 1.85-1.74 (m, 2H), 1.68-1.58 (m, 6H), 1.45 (s, 3H), 1.42 (s, 3H), 1.33-1.26 (m, 1H);

Compound N

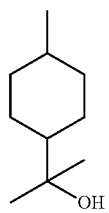

1H NMR (500 MHz, CDCl₃): δ 1.75 (ddd, J=16.6, 10.2, 4.5 Hz, 4H), 1.43-1.42 (m, 1H), 1.29-1.17 (m, 2H), 1.13 (s, 6H), 1.07-0.96 (m, 2H), 0.89 (dd, J=12.0, 2.9 Hz, 1H), 0.85 (d, J=6.5 Hz, 3H).

Bronchiectasis and Anti-Inflammation Experiment

Method: Isolated tracheal strip was fabricated, and was placed in the in-vitro tracheal experiment device; 100 µL acetylcholine chloride was added following tension adjustment and balancing to make the trachea extract, and the tension of trachea was increased. Once the tension was increased to the maximum value, and became balanced, corresponding trial drug was fed to inhibit extraction of the trachea; isometric muscle tension variation curve was recorded, and diastolic rate of smooth muscle was calculated. Diastolic rate=(tension after radiography−tension after dosing)/(tension after radiography)*100%.

Rat asthma model was established, and proceeded with blunt dissection of trachea following the last feeding of drug for trachea alveolar washing. Bronchi alveolar lavage fluid (BALF) was collected, and total number of nucleated cells were counted. Results were as shown in Table 2.

TABLE 2

| Group | | Relaxation rate % | | Inflammatory cell (× 10⁸/L) |
| --- | --- | --- | --- | --- |
| | R | 0.75 mmol/L | 1.25 mmol/L | |
| Blank group | | 7.73 ± 4.81 | 13.59 ± 9.14 | 85.50 ± 18.70## |
| Model group | | | | 182.50 ± 24.52ΔΔ |
| Aminophylline | | 43.67 ± 10.20ΔΔ | 56.70 ± 9.26ΔΔ | |
| Aᵃ | H | 14.62 ± 4.24* * | 21.57 ± 7.04* * Δ | |
| Bᵃ | CH₃ | 34.35 ± 14.72 | 47.72 ± 15.94 | |
| Cᵃ | CH₂CH₃ | 18.18 ± 6.26* * | 23.22 ± 4.39* * Δ | |
| Nᵃ | CH₂CH₂CH₃ | 21.20 ± 9.24* * | 25.47 ± 8.69* * | |
| ISOᵃ | CH₃–CH–CH₃ | 19.88 ± 8.82* * | 22.79 ± 8.27* * Δ | |
| TRᵃ | H₃C–C(CH₃)–CH₃ | 25.49 ± 6.53* | 28.02 ± 8.83* * | |
| α-T | | 28.40 ± 16.13ΔΔ | 38.35 ± 13.62Δ | 113.00 ± 21.27# |
| A | —(CH₂)₁₂CH₃ | 17.56 ± 2.89* *ΔΔ | 16.55 ± 14.47* * | 139.50 ± 31.24Δ |
| B | —(CH₂)₁₆CH₃ | 15.4 ± 9.83* * | 10.63 ± 13.77* * | 134.50 ± 25.27Δ |
| C | N(–)CH₂CH₂OH | 50.24 ± 7.30ΔΔ | 76.85 ± 7.70* *ΔΔ | 77.50 ± 68.81## |
| D | morpholinyl | 36.60 ± 13.79ΔΔ | 59.35 ± 14.66Δ | 110.5 ± 16.21### |

TABLE 2-continued

| Group | | Relaxation rate % 0.75 mmol/L | 1.25 mmol/L | Inflammatory cell (× 10⁸/L) |
|---|---|---|---|---|
| E | 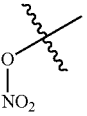 | 17.13 ± 6.98* * | 10.84 ± 4.46* * | 139.50 ± 20.71$^\Delta$ |
| F | 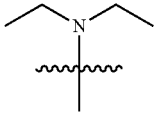 [SMILES: *N(CC)CC] | 42.33 ± 10.45$^{\Delta\Delta}$ | 46.71 ± 3.56* $^{\Delta\Delta}$ | 101.50 ± 14.68$^\#$ |
| G | 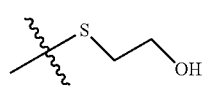 [SMILES: *SCCO] | 48.29 ± 9.36$^{\Delta\Delta}$ | 81.09 ± 10.15* *$^{\Delta\Delta}$ | 76.00 ± 18.15$^{\#\#}$ |
| H | 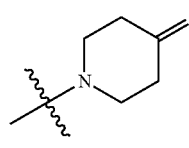 | 20.85 ± 7.55* *$^\Delta$ | 43.81 ± 10.16*$^{\Delta\Delta}$ | 123.00 ± 17.23$^\#$ |
| J | 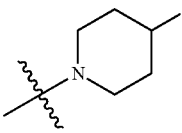 | 35.17 ± 13.87$^{\Delta\Delta}$ | 71.53 ± 15.45$^{\Delta\Delta}$ | 99.50 ± 21.23$^{\#\#}$ |
| K | 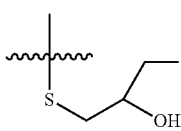 | 34.84 ± 19.74 | 65.29 ± 13.43$^\Delta$ | 104.50 ± 13.25$^{\#\#}$ |
| L | 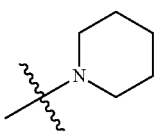 [SMILES: *N1CCCCC1] | 42.49 ± 6.14$^{\Delta\Delta}$ | 52.21 ± 6.98$^\Delta$ | 110.50 ± 16.18$^{\#\#}$ |
| M | 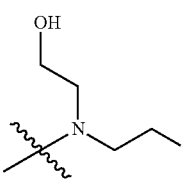 | 27.74 ± 2.08*$^{\Delta\Delta}$ | 61.01 ± 5.07$^{\Delta\Delta}$ | 97.50 ± 13.11$^{\#\#}$ |
| N |  | 27.16 ± 14.10* | 41.28 ± 13.17*$^{\Delta\Delta}$ | 140.00 ± 26.21$^\Delta$ |

With regard to several compounds in preferred embodiments of $^a$CN 103922927 A, formula for computation of diastolic rate has been improved to some extent; meanwhile, as there exists certain difference to testing results of different batches, data on diastolic rate is also varied.

" ︶︵︶ " refers to substitution position; compound N is product structure.

**refers to P<0.01 as compared with α-terpinenol group;

*refer to P<0.05 as compared with α-terpinenol group;

$^{\Delta\Delta}$refers to P<0.01 as compared with blank group;

$^\Delta$refers to P<0.05 as compared with blank group.

As compared with model group, $^\#$P<0.05, $^{\#\#}$P<0.01

Various compound groups can increase the diastolic rate of trachea smooth muscle, and inhibit inflammation under different dosage. On this account, it can be used to cure inflammation incurred by asthma, chronic obstructive pulmonary diseases and various other diseases, such as arthritis, rheumatoid arthritis, bronchitis, allergic rhinitis and allergic dermatitis.

Impact on Monocrotaline Incurred Pulmonary Hypertension to Rats

Method: Rat PAH model was established, and normal saline was fed to contrast group with volume equivalent to that for injection. Drug for interference was fed 2 days after radiography. 200 mg/Kg per compound was fed on daily basis. Normal saline was used with equivalent volume for lavage to the contrast group and model group respectively. Right ventricular systolic pressure of rat was measured by means of Right cardiac catheterization at anesthesia state on the 30th day. Results were as shown in Table 3.

TABLE 3

Right Ventricular Systolic Pressure of Different Groups ($\bar{x} \pm s$)

| | n | RVSP (mmHg) |
|---|---|---|
| Normal group | 10 | 21.08 ± 2.13$^{\Delta\#}$ |
| Model group | 8 | 43.78 ± 2.14$^{\#}$ |
| α-terpinenol group | 8 | 33.03 ± 2.22$^{\Delta}$ |
| A | 8 | 35.07 ± 2.81 |
| B | 10 | 36.08 ± 2.01 |
| C | 8 | 22.33 ± 1.03$^{\Delta\Delta\#\#}$ |
| D | 8 | 32.04 ± 1.12$^{\Delta}$ |
| E | 8 | 35.53 ± 3.02 |
| F | 8 | 23.35 ± 1.04$^{\Delta\Delta\#\#}$ |
| G | 8 | 21.08 ± 1.31$^{\Delta\Delta\#}$ |
| H | 8 | 30.33 ± 2.03$^{\Delta}$ |
| J | 8 | 27.06 ± 1.17$^{\Delta}$ |
| K | 8 | 31.13 ± 2.03$^{\Delta}$ |
| L | 8 | 25.36 ± 1.17$^{\Delta\Delta\#}$ |
| M | 8 | 33.36 ± 2.05$^{\Delta}$ |
| N | 8 | 32.56 ± 2.82$^{\Delta}$ |

As compared with model group, $\Delta P<0.05$, $\Delta\Delta P<0.01$; as compared with α-terpinenol group $\#P<0.05$, $\#\#P<0.01$.

As indicated by testing results, various compounds can provide certain protection for monocrotaline incurred rat pulmonary artery hypertension. Furthermore, they can improve hemodynamic indicators, reduce right ventricular systolic pressure, alleviate right ventricular load, reduce right heart hypertrophy indicators, and alleviate pulmonary vascular remodeling.

The invention claimed is:

1. A terpinenol compound, characterized in that its structure is as shown in Formula (I):

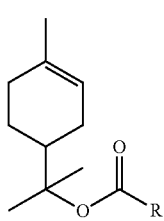

(I)

wherein R is one of the following functional groups:

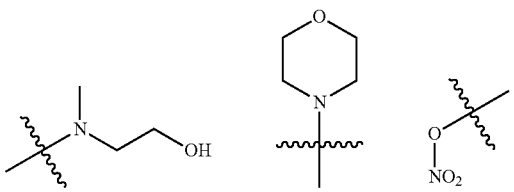

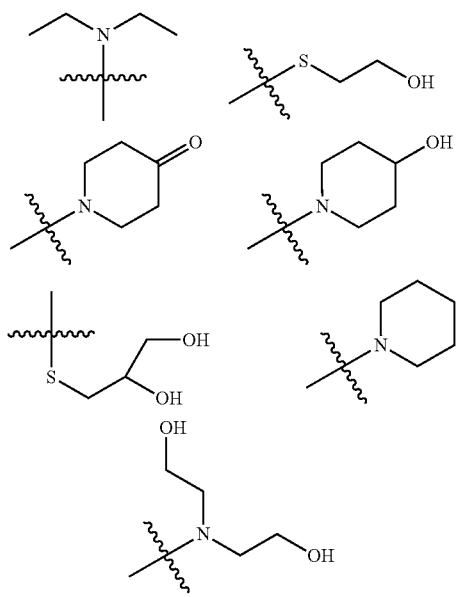

and wherein, "⌇" refers to link location.

2. The method for preparation of terpinenol compound according to claim 1, characterized in that it comprises the following steps:

(1) obtaining the esterified intermediate through reaction between the α-terpinenol and bromoacetyl bromide in the dichloromethane under the action of pyridine;

(2) obtaining the terpinenol compound through substitution reaction between the esterified intermediate as obtained in Step (1) and nucleophilic reagent in the acetonitrile under the action of inorganic base;

wherein the nucleophilic reagent is in one of the following structural groups:

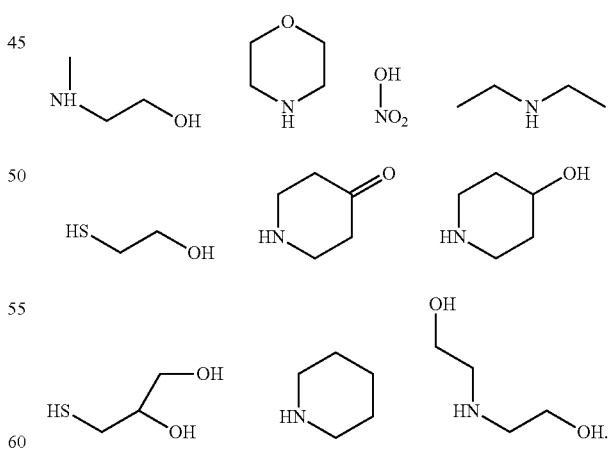

3. A method of treating or alleviation of asthma, inflammation or pulmonary hypertension in a subject comprising the step of administering an effective amount of a terpinenol compound to the subject; wherein the terpinenol compound's structure is as shown in Formula (I):

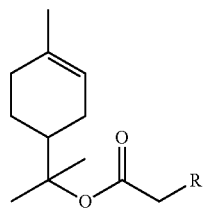
(I)
wherein R is one of the following functional groups:
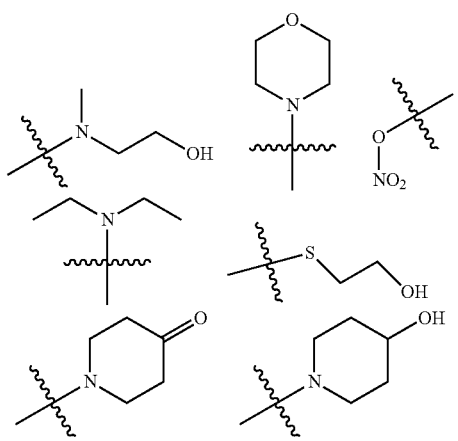
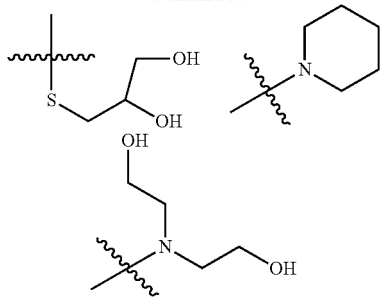
and wherein,
" ~~~ "
refers to link location.
4. The method according to claim 3, wherein R is
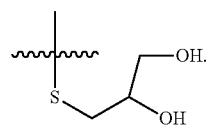 [SMILES: *SCC(O)CO]
* * * * *